United States Patent [19]

Townsend et al.

[11] 4,343,741
[45] Aug. 10, 1982

[54] CHIRAL PHOSPHINES

[75] Inventors: John M. Townsend, Morris, Conn.; Donald Valentine, Jr., Santa Clara, Calif.

[73] Assignee: Hoffmann-La Roche Inc., Nutley, N.J.

[21] Appl. No.: 256,378

[22] Filed: Apr. 22, 1981

[51] Int. Cl.³ .................. C07D 207/10; C07D 307/32
[52] U.S. Cl. ..................................... 548/412; 548/531
[58] Field of Search .............. 260/326.4, 326.22, 343.6

[56] References Cited

U.S. PATENT DOCUMENTS 3,883,580  5/1975  Solodar ............................... 560/164
3,980,670  9/1976  Kummer et al. .................. 260/343.6
4,008,281  2/1977  Knowles et al. .............. 260/429 CY
4,123,465  10/1978  Valentine .............................. 568/13

OTHER PUBLICATIONS

Achiwa, Chem. Lett., pp. 297–298, (1978).
Achiwa; J.A.C.S., vol. 98, pp. 8265–8266, (1976).
Achiwa; Tet. Letters, No. 50, pp. 4431–4432, (1977).
Ojima et al; J. Org. Chem., vol. 43, pp. 3444–3446, (1978).

*Primary Examiner*—Mary C. Lee
*Attorney, Agent, or Firm*—Jon S. Saxe; George M. Gould; John B. Wilson

[57] ABSTRACT

Novel substituted diphenyl tertiary phosphines of a pyrrolidine carboxylic acid derivative and their use as catalysts in the enantioselective hydrogenation of α-keto-β,β-dimethyl-γ-butyrolactone.

15 Claims, No Drawings

CHIRAL PHOSPHINES

BACKGROUND OF INVENTION

In the past, rhodium complexes of the ditertiary phosphine of the formula:

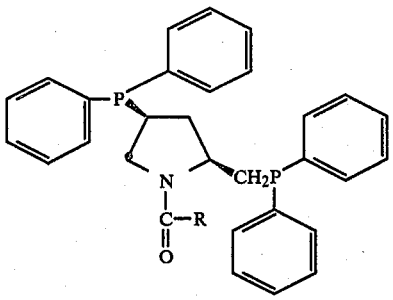

II where R is tertiarybutoxy, have been used as catalysts in the enantioselective hydrogenation of α-keto-β,β-dimethyl-γ-butyrolactone which has the formula:

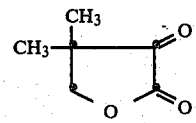

III to R-(—)-pantolactone which has the formula:

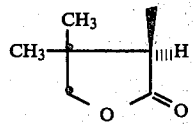

IV

See Achiwa et al., *Tetrahedron Letters*, No. 50, 4431 (1977); Ojima, *J. Org. Chem.*, 43, 3444 (1978); and Achiwa, *Chem. Lett.* 297 (1978).

For certain uses of the compound of formula IV as a pharmaceutical, it is necessary to produce this compound with the correct epimeric configuration of the chiral carbon atom. Therefore, it is necessary to use a catalyst which effects a highly enantioselective hydrogenation of the ketolactone precursor of formula III. It is also desired to find a catalyst that will carry out this hydrogenation quickly and efficiently. Since the rhodium complex catalyst is relatively expensive, it has been desired to find a hydrogenation catalyst that will not be destroyed during the reaction and can easily be recovered from the reaction medium. It is these properties which will provide a catalyst that can be reused for many hydrogenation procedures.

While pantolactone has been obtained in optically active form by resolution, the catalytic asymmetric synthesis has proven to be more effective from a commercial standpoint. To optimize catalytic assymetric synthesis, there has been a need for catalysts which can provide high yields, fast rates and use low catalyst loadings.

SUMMARY OF INVENTION

In accordance with this invention, it has been discovered that compounds of the formula:

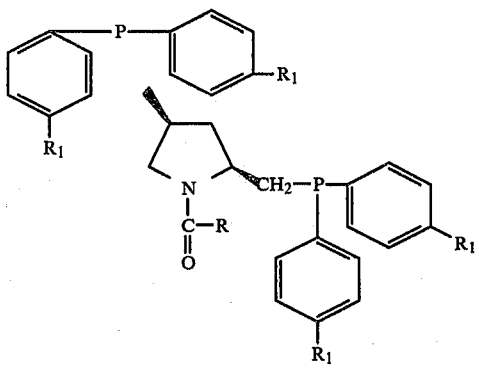

I where R is as above, $R_1$ is lower alkyl, lower alkoxy or

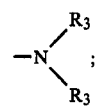

and $R_3$ is lower alkyl form rhodium complexes which are effective catalysts for the enantioselective hydrogenation of a compound of formula III to a compound of formula IV. The rhodium complex produced from the compound of formula I is an effective catalyst for the hydrogenation of the compound of formula III. The catalyst of this invention is not poisoned during the reaction and can be recovered from the reaction medium so that it can be utilized for subsequent hydrogenations. Therefore, the compounds of this invention provide effective catalysts for the preparation of pantolactone of formula IV by enantioselective hydrogenation.

DETAILED DESCRIPTION

The term "lower alkyl" designates saturated straight or branched chain aliphatic hydrocarbons containing from 1 to 7 carbon atoms such as methyl, ethyl, propyl, n-butyl, tertiary butyl etc. The term "lower alkoxy" denotes lower alkoxy groups containing from 1 to 7 carbon atoms such as methoxy, ethoxy, isopropoxy, n-butoxy, etc.

Among the preferred compounds of formula I are those compounds where $R_1$ in the compound of formula I is lower alkyl. The preferred lower alkyl groups are methyl and ethyl. Where $R_1$ in the compound of formula I is lower alkoxy, the preferred lower alkoxy group is methoxy and ethoxy.

The term "halogen" as used throughout the specification designates any conventional halogen group such as chlorine, iodine or bromine with chlorine being preferred.

In the schematic representation of molecular structures, the wedge ( ▲ ) indicates that the substituent is above the plane of the molecule, the broken line ( ≡ ) indicates that the substituent is below the plane of the molecule.

The compounds of formula I are formed by the reaction of a lithium phosphide of the formula:

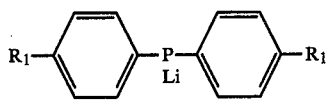

with a compound of the formula:

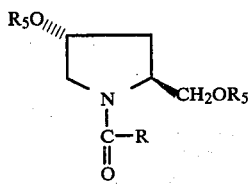

wherein R is as above and $R_5$ is a leaving group.

In the compound of formula VIII, $R_5$ is a leaving group preferably tosyl(p-toluenesulfonyl) or mesyl(methanesulfonyl). The reaction of the compound of formula VII with a compound of formula VIII is carried out in an ether solvent. Any conventional ether solvent can be used in this reaction. Among the preferred ether solvents are tetrahydrofuran, diethyl ether, dioxane, etc. In carrying out this reaction, temperatures and pressures are not critical and this reaction can be carried out at room temperature and atmospheric pressure. On the other hand, elevated or reduced temperatures and pressure can be utilized. Generally, it is preferred to carry out this reaction at a temperature of from $-50°$ to $50°$ C. This reaction is carried out by reacting 2 mols of the compound of formula VII with the compound VIII to produce the compound of formula I. The compound of formula VII may be present in the reaction medium in excess of 2 mol of the compound of formula VIII.

The compound of formula VIII is prepared by forming the ditosylate or dimesylate from the diol of formula:

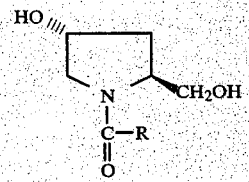

Any conventional method of converting a hydroxy substituent to a mesylate or tosylate can be used for carrying out this conversion.

The compound of formula VII is prepared from a compound of the formula:

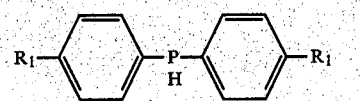

wherein $R_1$ is as above by reacting the compound of formula IX with a lower alkyl lithium, preferably n-butyl lithium. Any conventional method of converting a hydride to a lithium compound can be used. Generally, it is preferred to carry out this reaction in an ether solvent at temperatures of from $-50°$ to $+50°$ C. The preferred ether solvent for use in this reaction is tetrahydrofuran.

The compounds of formula IX are generally known. They can be prepared from compounds of the formula:

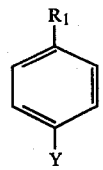

wherein $R_1$ is as above, and Y is halogen via the corresponding phosphine oxides of the formula:

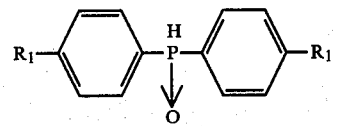

In the first step, the halide of formula X is converted to magnesium halide salts of the compound of formula X. Any method conventionally employed in converting a halide to a Grignard reagent can be used. On the other hand, the compound of formula X can be converted to corresponding lithium compounds of formula X by treatment with a lower alkyl lithium such as described hereinbefore. The Grignard reagent or the lithium compound of formula X is converted to the compound of formula XI by reaction with a dialkyl or diaryl phosphite of the formula:

wherein $R_6$ is lower alkoxy or phenoxy the preferred phosphate of formula XII is dibutylphosphite.

The compound of formula X either as the lithium compound or the Grignard reagent can be reacted with the phosphine oxide of formula XII to produce the compound of formula XI. This reaction can be carried out in the presence of an ether solvent. Any conventional ether solvent can be utilized. Among the preferred ether solvents are tetrahydrofuran and diethyl ether. Generally this reaction can be carried out at a temperature of from $-50°$ C. to $+50°$ C. In carrying out this reaction, at least 2 mol of the compound of formula X either as the Grignard salt or the lithium compound is reacted with one mol of the compound of formula XI.

The compound of formula XI thus produced is converted to phosphine of formula IX by treating with a reducing agent. Any of the reducing agents conventionally used for converting phosphine oxides to phosphines can be utilized in carrying out this reaction. Among the preferred reducing agents are the trihalosilane reducing agents such as trichlorosilane. Other reducing agents which can be used include lithium aluminum hydride. Any of the conditions conventional in using these reducing agents can be used in the conversion of the compound of formula XI to the compound of formula IX.

In accordance with another embodiment of this invention, the compound of formula IX can be formed from the compound of formula

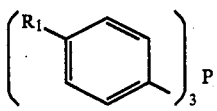 XIV wherein $R_1$ is as above.

by treating the compound of formula XIV with lithium to form the compound of Formula VII. In the next step, the compound of formula VII is hydrolyzed with water to form the compound of formula IX. In view of the fact that formula XIV is a commercial product, this conversion provides an effective means for forming the compound of formula IX. Furthermore, this procedure removes many of the impurities which are present in commercial preparations of the compound of formula XIV.

The catalysts used herein are soluble coordinating complexes of the chiral tertiary phosphine of the formula I and rhodium. The complexes can be prepared by simply mixing the compound of formula I with a rhodium liberating compound to produce the compound of formula I. Any conventional rhodium liberating compound can be used in providing the complex. Typical rhodium liberating compounds that can be used include rhodium trichloride hydrate, rhodium tribromide hydrate, rhodium sulfate, organic rhodium complexes with ethylene, propylene, etc., bisolefins such as 1,5-cyclooctadiene and 1,5-hexadiene, bicyclo-2.2.1-hepta-2,5-diene and other dienes which can form bidentate agents or an active form of metallic rhodium that is readily solubilized. Among the preferred rhodium liberating compounds are $\mu,\mu'$-dichlorobis-[1,5-cyclo octadiene rhodium (I)], hydrated rhodium tribromide as well as $\mu,\mu$-dichlorobis[(norbornadiene)rhodium (I)] and $\mu,\mu'$-dichlorobis-[bis(olefin)rhodium (I)] where the olefin may be ethylene, propylene, cyclooctene, etc. The use of rhodium liberating compounds for forming chiral tertiary phosphine rhodium complexes is disclosed in U.S. Pat. No. 4,123,465, Valentine, U.S. Pat. No. 3,883,580, Soldar; and U.S. Pat. No. 4,008,281, Knowles et al.

It has been found that the catalysts and processes of this invention which are preferable are those where the optically active bis phosphine of formula I is present in a ratio of about 0.5 to about 10, preferably 1.0 mols to 2 mols per mole of the rhodium metal. Preferably, the rhodium complex of the compound of formula I is formed in situ during the hydrogenation reaction.

The process of this invention allows the keto group in the lactone of formula III to be hydrogenated enantioselectively to the hydroxy group in the compound of formula IV. The hydrogenation reaction is generally carried out in an ether solvent. Any of the conventional ether solvents such as those mentioned herein before can be utilized. In carrying out this reaction, the catalysts used is the rhodium complex of the compound of formula I. This rhodium complex can be formed in situ from the rhodium liberating compound and the phosphine of formula I during the reaction. In this case, the rhodium liberating compound and the compound of formula I are added to the reaction medium prior to hydrogenation. Generally, it is preferred to dissolve the rhodium liberating compound and the phosphine of formula I in an amount so that from about 0.5 to 10 mols of rhodium are provided per mol of the compound of formula I. On the other hand, the rhodium complex can be formed prior to the hydrogenation reaction in the manner described above and added to the reaction medium utilized for hydrogenation. When the catalyst is added, it may be added to the reaction medium prior to or at the same time as the compound of formula III. The components for the preparation of the catalysts are the rhodium liberating compounds and the optically active phosphine of formula I and can be added, prior to hydrogenation, with the compound of formula III. The catalysts can be added in any effective catalytic amount and generally in the range of about 0.0001% to about 5% by weight of contained rhodium based upon the weight of the compound of formula III. A preferred concentration range is from about 0.0002% to about 0.5% of the rhodium contained in the catalyst based upon the weight of the compound of formula III.

In carrying out the hydrogenation reaction, any conventional inert organic solvent can be utilized. Among the preferred solvents are the ether solvents such as dioxane, diethyl ether, tetrahydrofuran, etc. After the addition of the components to the solvent, hydrogen is added to the mixture in an amount of from about 1 to 10 times the mol quantity of the compound of formula III or in an amount necessary to complete the hydrogenation to the point desired. The pressure of the system will necessarily vary since it will depend upon the size of the hydrogenation apparatus, amounts of components and amounts of solvent. Generally, it is preferred to use a pressure of from 1 atmosphere to 50 atmospheres with pressures of from 2 atmospheres to 50 atmospheres being preferred. In carrying out this hydrogenation, temperatures and pressures are not critical and this reaction can be carried out at room temperature. On the other hand, higher and lower temperatures can be utilized. Generally, it is preferred to carry out this reaction at either room temperatures (20° C.) or temperatures above room temperature such as from 35° C. to 90° C.

Upon completion of the reaction, the solvent can be removed from the product and the catalyst. The product and the catalyst are separated by conventional means.

The following Examples are illustrative but not limitative of the instant invention. All temperatures are in degrees centigrade.

EXAMPLE 1

A 500-mL, 3-neck flask equipped with a mechanical stirrer, addition funnel and argon inlet was flame-dried, cooled under argon, and charged with 230 mL of tetrahydrofuran. Under a stream of argon, 1.5 g (0.214 g atom) of lithium wire was cut into small pieces directly into the reaction flask. The addition funnel was charged with a solution of 15.2 g (0.05 mol) of tri(p-tolyl)phosphine in 120 mL of tetrahydrofuran. The phosphine solution was added dropwise over 25 min. at ambient temperature and the mixture was stirred for 7 h. A sample of the red-brown mixture was examined by GLC (gas liquid chromatography) which indicated the cleavage to be ca. 85% complete. The mixture was treated with 1.38 g (0.025 mol) of ammonium chloride and the now red-orange mixture was allowed to stir an additional 12 h. Via cannula, the solution was transferred under argon into a 1-neck flask containing 2.0 g (0.11 mol) of water. The now colorless solution was stripped of solvents on the rotary evaporator (previously flushed with argon) at 60°/5-100 mm Hg using a mechanical vacuum pump. The flask was attached to a bulb to bulb distillation apparatus and the thick milky residue was distilled at 135°-55°/0.06 mm Hg to give 8.8 g (82%) of colorless oil which by GLC (gas liquid chromatography) was 97% bis(p-tolyl)-phosphine and 3% tri(p-tolyl)phosphine. The oil was redistilled on the bulb to bulb distillation apparatus at 100°-15°/0.06 mm Hg to give 8.2 g (76%) of pure (100% by GLC) bis(p-tolyl)phosphine.

EXAMPLE 2

A 500-mL, 3-neck flask equipped with a thermometer, addition funnel and argon inlet was flame-dried, cooled under argon, and then charged with a solution of 6.0 g (0.0277 mol) of freshly distilled bis(p-tolyl)phosphine in 180 mL of tetrahydrofuran. The solution was cooled to 5°-10° and treated over 5 min. with 11.5 mL (0.0282 mol) of 2.45 M n-butyl lithium lithium solution. The now deep red solution was treated dropwise over 30 min. at 10°-15° C. with a solution of 5.82 g (0.0111 mol) of ditosylate, i.e. 2S,4R-1-carbotertiarybutoxy-4-p-toluenesulfonyloxy-2-(p-toluenesulfonyloxymethyl)-pyrrolidine in 25 mL of tetrahydrofuran. Stir under argon for 12 h (overnight). The mixture was treated with 2.0 g (0.037 mol) of ammonium chloride and stirred for 10 min. to discharge the color. The pale yellow solution was transferred via cannula under argon to a 1-neck flask and then stripped of solvent on the rotary evaporator at 50°/3-5 mm Hg. The residue was treated with 50 mL of toluene and 25 mL of water and stirred vigorously for 10 min. The toluene layer was removed by cannula under argon and the aqueous layer was further extracted with 3×50 mL of toluene. The combined toluene layers were dried with 15 mL of brine followed by 20 g of anhydrous sodium sulfate. The solution was transferred to another flask by cannula through a filter plug of cotton, and the toluene was removed on the rotary evaporator at 65°/5 mm Hg (mechanical vacuum pump) to give 8.42 g of thick oily residue. The residue was placed in a bulb to bulb distillation apparatus and heated to 100°-105°/0.02-0.04 mm Hg for 2 h to give 0.635 g of distillate and 6.75 g residue of crude product. The residue was chromatographed on 100 g of silica gel, eluting with 450 mL of toluene:acetone (29:1 parts by volume). Intermediate fractions were stripped of solvent on the rotary evaporator to give 5.8 g (86%) of crude product as a colorless glass. The TLC at this point still indicated the presence of polar impurities. Crystallization of 700 mg of this material from 3 mL of absolute ethanol gave 400 mg colorless crystals, mp 100°-104° (sealed tube). One additional crystallization from absolute ethanol (1.4 mL) was required to give [2S,4S]-4-[(4,4'-dimethyldiphenyl)phosphino]-2-[[(4,4'-dimethyldiphenyl)phosphino]methyl]-1-pyrrolidine carboxylic acid 1,1-dimethyl ethyl ester without impurities detectable by TLC (mp 102°-104°, 332 mg, equivalent to a 41% overall yield) and two additional crystallizations were required to give this product (160 mg) of constant melting point: mp 106°-109° (sealed tube); $[\alpha]_D^{25}$ −35.5° (c 0.6, benzene). The remainder of the 5.8 g crude product obtained after chromatography provided 2.2 g (35% overall) of pure product, mp 104°-108°, after several crystallizations from absolute ethanol, as well as additional material (ca. 2.0 g) of slightly lower quality as judged by mp or TLC (thin layer chromatography).

EXAMPLE 3

Bis-(4-methoxyphenyl)phosphine

A solution-suspension of 1.4 g (5.34 mmol) of bis(4-methoxyphenyl)phosphine-oxide in 18 mL of toluene was treated under argon with 3.35 g (2.5 mL, 25 mmol) of trichlorosilane in one portion. This resulted in moderate heat and gas evolution and led to complete solution of the phosphine oxide. The mixture was heated at 90° for 5 h, whereupon the clear colorless solution was cooled to 0°. With vigorous stirring, 8.0 mL of 2 N aqueous sodium hydroxide solution (16 mmol) was added slowly while cooling the mixture in an ice-bath to moderate the vigorous reaction. When all the sodium hydroxide had been added, the mixture was allowed to warm to room temperature and stirred vigorously until all solid dissolved (30-90 min), leaving two clear, colorless liquid phases. The layers were allowed to separate and the toluene layer was drawn off under argon via a cannula. The aqueous layer was extracted with 2×20 mL of toluene. The combined toluene extracts were dried (deoxygenated brine and sodium sulfate), filtered, and stripped of solvent on the rotary evaporator at 80°/5 mm Hg to give 1.11 g (84.5%) of crude product. The thick oil was distilled by bulb to bulb distillation at 115°-135°/0.02 mm Hg for 1 h to give 0.747 g (57%) of bis-(4-methoxyphenyl)phosphine as a colorless thick oil which shortly crystallized to colorless, slightly greasy crystals.

EXAMPLE 4

A flame-dried, 100-mL, 3-neck round bottom flask equipped with a thermometer, argon inlet and glass stir bar for magnetic stirring was charged with 50 mL of tetrahydrofuran (THF) and 0.70 g (2.84 mmol) of freshly distilled bis-(4-methoxyphenyl)phosphine. The solution was cooled to 5° C. and 1.15 mL (2.84 mmol) of 2.45 M n-butyl lithium solution in hexane. The orange-red solution was immediately treated at 5° with a solution of 0.392 g (0.74 mmol) of 2S,4R-1-carbotertiarybutoxy-4-p-toluenesulfonyloxy-2-(p-toluenesulfonyloxymethyl)pyrrolidine in 10 mL of THF. The mixture was stirred for 10 min and then quenched by the addition of 0.50 g (9.4 mmol) of ammonium chloride. The deep red mixture gradually turned to pale yellow upon stirring for 10 min. The mixture was stripped of solvents on the rotary evaporator at 40°-50°/5 mm Hg. The residue was treated with 20 mL of toluene and 10 mL of water. The toluene layer was removed by cannula under argon and the aqueous layer was further extracted with 2×20 mL of toluene. The combined toluene layers were dried with 20 mL of brine followed by 2 g of anhydrous sodium sulfate. The solvent was removed on the rotary evaporator at 80°/5 mm Hg to give 0.71 g oily residue. The residue was placed on the bulb to bulb distillation reaction and heated at 125°-135°/0.015 mm Hg for 2 h to give 0.277 g of distillate and 0.426 g residue of crude product. The residue was chromatographed on 25 g of silica gel, eluting with 225 mL of toluene:acetone (29:1 parts by volume). Intermediate fractions were stripped of solvent on the rotary evaporator and the residual colorless oil was crystallized from 4 mL of absolute ethanol. There was obtained 0.06 g (12%) of colorless crystals of the product [2S,4S]-4-[(4,4'-dimethoxydiphenyl)phosphine]-2-[[(4,4'-dimethoxydiphenyl)phosphine]methyl]-1-pyrrolidine-1-carboxylic acid 1,1-dimethylethyl ester, mp 118°–123°. Once seed crystals had been obtained, additional product was obtained from impure chromatography fractions by crystallization from absolute ethanol. Analytically pure product had mp 121°–124°; $[\alpha]_D^{25}$ −39.1° (c 0.6, benzene).

EXAMPLE 5

Bis-(4-dimethylaminophenyl)phosphine oxide

A solution of 20 g (0.1 mol) of p-bromo-N,N-dimethylaniline in 150 mL of anhydrous ether was treated dropwise over 1 h at 0°–5° with a solution of 40 mL of 2.45 M n-butyl lithium in hexane (0.1 mol) in 50 mL of anhydrous diethyl ether. The mixture was stirred at 0.5° for 1¼ h and then allowed to warm to 22°. An additional 1.0 mL of n-butyl lithium solution was added. The mixture was connected to a vacuum line and a distillation receiver bulb cooled in a dry ice bath. The solvents and volatile by-products were removed in vacuo (mechanical pump) at 15°–20°, leaving a pale cream powder of 4-dimethylaminophenyl lithium reagent. The solid was pulverized under argon in the same flask and then further pumped in vacuo at 25° for 20 minutes to remove all volatiles. The lithium reagent was then dissolved in 150 mL of anhydrous ether and treated rapidly with a solution of 5.8 g (5.8 mL×0.03 mol) of di(n-butyl)phosphite in 50 mL of anhydrous ether at 5°–10°. The resulting white slurry was treated with 50 mL of tetrahydrofuran, and the resulting colorless solution was allowed to stir for 12 h at 23°. The mixture was then poured into 200 mL of water and adjusted to neutral pH with a few drops of dilute aqueous sulfuric acid. The organic layer was separated, the aqueous layer was extracted once with 75 mL of diethyl ether, and the combined ether layers were washed (brine) and dried (sodium sulfate) and stripped of solvent to give the crude product as a colorless oil. Addition of 50 mL of fresh ether caused precipitation of 6.6 g (76%) of bis-(4-dimethylaminophenyl)phosphine oxide as a colorless solid, mp 140°–165°. Two recrystallizations from benzene gave 3.1 g (36%) of analytically pure product, mp 150°–170° (in air).

EXAMPLE 6

Bis-(4-dimethylaminophenyl)phosphine

A solution-suspension of 4.0 g (13.9 mmol) of bis(4-dimethylaminophenyl)phosphine oxide in 100 mL of toluene was treated with 16.08 g (12 mL, 120 mmol) of trichlorosilane in one portion. The mixture was stirred at 50°–80° for 18 h and remained a white slurry throughout. The mixture was cooled to 15° to an ice bath and treated slowly with 100 mL of 5 N sodium hydroxide solution. After complete addition, the mixture was stirred vigorously for 2 h, to yield two clear, colorless liquid phases. The toluene layer and 2×50 mL toluene extracts were separated, washed and dried as described in Example 4. Solvent removal on the rotary evaporator (mechanical pump vacuum) gave 3.5 g (93%) of crude product as a colorless solid. Distillation on the bulb to bulb distillation apparatus at 195°–200°/0.2 mm Hg gave 3.0 g (79%) of colorless crystals, mp 116°–125° (sealed tube) of the product bis-(4-dimethylaminophenyl)phosphine. Just before use as described below, the product was redistilled on the bulb to bulb distillation apparatus at 165°–170°/0.015 mm Hg to give 2.7 g of the product as colorless crystals, mp 80°–90° (sealed tube).

EXAMPLE 7

A 500-ml, 3-neck round bottom flask was fitted with a mechanical stirrer, thermometer, and Claisen head holding an addition funnel and an argon inlet. The apparatus was flame-dried and cooled under argon. The flask was charged with 2.7 g (10.0 mmol) of bis-(4-dimethylaminophenyl)phosphine and 150 mL of tetrahydrofuran (THF). The solution was cooled to −5° and treated with 5.2 mL of 2.8 M n-butyllithium solution in hexane over 2–3 min. Immediately after this addition, a solution of 2.4 g (4.57 mmol) of 2S,4R-1-carbotertiarybutoxy-4-p-toluenesulfonyloxy-2-(p-toluenesulfonyloxymethyl)pyrrolidine in 50 mL of THF was added at such a rate that the temperature remained at 0°±5°. The reaction was allowed to warm to 20° and then quenched by the addition of 1 mL of water. The mixture was then transferred to a 1-neck flask via cannula under argon and the solvents were removed on the rotary evaporator at 40°/3–5 mm Hg. The residue was treated with 30 mL of water and extracted with 3×80 mL portions of toluene. The toluene extracts were combined, washed with 15 mL brine and dried over 10 g of sodium sulfate. Solvent removal on the rotary evaporator at 50°/3–5 mm Hg gave 3.6 g of crude product as a thick yellow oil. The oil was dissolved in 30 mL of warm absolute ethanol and upon cooling, the solution deposited 1.5 g (45%) of the product [2S,4S]-4-[[4,4′-(dimethylamino)-diphenyl]phosphino]]-2-[[4,4′-dimethylamino)diphenyl]phosphino]methyl]pyrrolidine-1-carboxylic acid 1,1-dimethylethyl ester as colorless crystals, mp 138°–142° (sealed tube). Recrystallization from 110 mL of absolute ethanol gave 1.1 g of crystals, mp 120°–24° (sealed tube). A final crystallization from 60 mL of absolute ethanol gave 0.90 g (27%) of pure product, mp 115°–17° (sealed tube); $[\alpha]_D^{25}$ −54.27° (c 0.6, benzene).

EXAMPLE 8

Under anaerobic conditions in our dry box a 100-ml one-neck flask was charged with 0.0043 g (9.33×10$^{-6}$ mol) of μ,μ′-dichlorobis[(norbornadiene)rhodium (I)], 0.017 g (27.9×10$^{-6}$ mol) of [2S,4S]-4-[(4,4′-dimethyldiphenyl)phosphino]-2-[[(4,4′-dimethyldiphenyl)phosphino]methyl]-1-pyrrolidine carboxylic acid 1,1-dimethylethyl ester and 5 ml of tetrahydrofuran (THF). The solution was stirred for 5 min and then treated with 30.0 g (0.234 mol) of the ketolactone α-keto-β,β-dimethyl-λ-butyrolactone and 20 ml of THF. The flask was sealed with rubber serum stopper secured with copper wire and the bright yellow slurry was removed from the dry box. Using a hot air dryer (heatgun), the flask was warmed gently to ca. 30°–35° until complete solution of the ketolactone occurred (ca. 5 min). Using a double-pointed stainless steel cannula, the warm solution was transferred from the flask under positive argon pressure into a 100 ml stainless steel reactor. The reactor had previously been evacuated and refilled with argon several times and left under a low positive pressure or argon. The reactor was sealed and pressurized to 130 kg/cm$^2$ with H$_2$. After ensuring that the system was leakfree, the reaction was heated to 60° and stirred at 60° under 130–132 kg/cm$^2$ for 70 hr. The reaction was then cooled and vented, and the reaction mixture removed. The solvent was removed on the rotary evaporator at 30° to give 32.38 g (106%) of solid residue still containing some solvent. The residue was subjected to bulb-to-bulb distillation (Kugelrohr) using receiver bulbs cooled to −10°. After removal of a forerun composed primarily of THF crystalline crude R-(−)-pantolactone was collected at 95°–105°/0.07 mm Hg; 28.95 g (95.0%); mp 88°–90°; $\alpha_D^{25}$ −16.61° (c 1, absolute ethanol), (optical purity 77.3%). The crude R-(−)-pantolactone was recrystallized from 25 ml of ethyl acetate by allowing the boiling solution (volume 50 ml) to cool undisturbed to ca. 45°, seeding it with a few crystals of authentic product, and cooling it to room temperature and finally in the refrigerator at 0°. Filtration provided: 1st crop: 17.65 g (57.9%), mp 88°–90°; $\alpha_D^{25}$ −19.9° (c 1, absolute ethanol) (opt. purity 93%), 2nd crop: 5.68 g (18.6%) by concentration of mother liquors. mp 84°–86°; $[\alpha]_D^{25}$ −17.1° (c 1. absolute ethanol) (optical purity 79.7%).

The two crystal crops were combined and recrystallized from 30 ml of ethyl ether as described above: 1st crop: 21.15 g (69.4%) mp 91°–92°; $\alpha_D^{25}$ −21.5° (c 1, absolute ethanol) (optical purity ca. 100%); $\alpha_D^{25}$ −50.0° (c 1, water) (optical purity 99%). The mother liquors here were combined with that resulting from the ethyl acetate crystallization and concentrated to give 7.2 g of pantolactone suitable for reoxidation to ketolactone.

EXAMPLE 9

Under anaerobic conditions in our dry box a 100-mlone-neck flask was charged with 0.0043 g of μ,μ'-dichlorobis [(norbornadien)rhodium(I)], 0.017 g of [2S,4S]-4-[(4,4'-dimethoxydiphenyl)phosphinol]2-[[(4,4'-dimethoxydiphenyl)phosphino]methyl]1-pyrrolidine carboxylic acid 1,1-dimethylethyl ester, and 5 ml of tetrahydrofuran. The solution was stirred for 5 min and then treated with 30.0 g of the ketolactone α-keto-β,β-dimethyl-γ-buyrolactone and 20 ml of THF. The flask was sealed with a rubber serum stopper secured with copper wire and the bright yellow slurry was removed from the dry box. Using a hot air dryer (heatgun), the flask was warmed gently to ca. 30°–35° until complete solution of the ketolactone occurred (ca. 5 min). Using a double-pointed stainless steel cannula, the warm solution was transferred from the flask under positive argon pressure into a 100 ml stainless steel reactor. The reactor had previously been evacuated and refilled with argon several times and left under a low positive pressure of argon. The reactor was sealed and pressurized to 130 kg/cm² with H₂. After ensuring that the system was leakfree, the reaction was heated to 60° and stirred at 60° under 130–132kg/cm² for 70 hr. The reaction was then cooled and vented, and the reaction mixture removed. The solvent was removed on the rotary evaporator at 30° to give 32.38 g (106%) of solid residue still containing some solvent. The residue was subjected to bulb-to-bulb distillation (Kugelrohr) using receiver bulbs cooled to −10°. After removal of a forerun composed primarily of THF, crystalline crude R-(−)-pantolactone was collected at 95°–105°/0.07 mm Hg: 28.95 g (95.0%); mp 88°–90°; $[\alpha]_D^{25}$ −12.63° (c 1, absolute ethanol), (optical purity 56.9%). This crude pantolactone is purified in the manner described in Example 8.

EXAMPLE 10

The procedure of Example 9 was carried out except that the phosphino compound was [2S,4S]-4-[[4,4'-(dimethylamino)diphenyl]phosphino]-2-[[[4,4-(dimethylamino)diphenyl]phosphino]methyl]pyrrolidine-1-carboxylic acid 1,1-dimethylethyl ester, bulb-to-bulb distillation yielded crude R-(−)-pantolactone of $[\alpha]_D^{25}$ −14.29° (c=1, b, ethanol, optical purity 64.4%). The crude pantolactone is purified in the manner of Example 8.

We claim:

1. A compound of the formula:

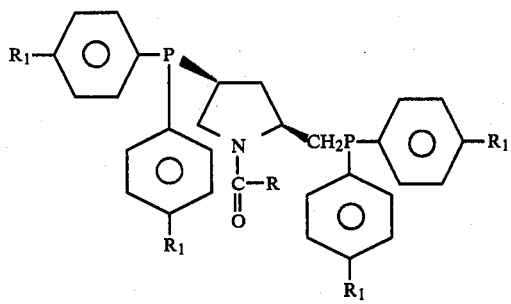

wherein R is tertiarybutoxy, and R₁ is lower alkyl, lower alkoxy or

and R₃ is lower alkyl.

2. The compound of claim 1 wherein said compound is [2S,4S]-4-[(4,4'-dimethyldiphenyl)phosphino]-2-[[(4,4'-dimethyldiphenyl)phosphino]methyl]-1-pyrrolidine carboxylic acid 1,1-dimethylethyl ester.

3. The compound of claim 1 wherein said compound is [2S,4S]-4-[[4,4'-(dimethylamino)-diphenyl]phosphino]-2-[[4,4'(dimethylamino)diphenyl]phosphino]methyl]pyrrolidine-1-carboxylic acid 1,1-dimethylethyl ester.

4. The compound of claim 1 wherein said compound is [2S,4S]-4-[(4,4'-dimethoxydiphenyl)phosphino]-2-[[(4,4'-dimethoxydiphenyl)phosphino]methyl]-1-pyrrolidine-1-carboxylic acid 1,1-dimethylethyl ester.

5. A complex of rhodium with an optically active phosphine of the formula:

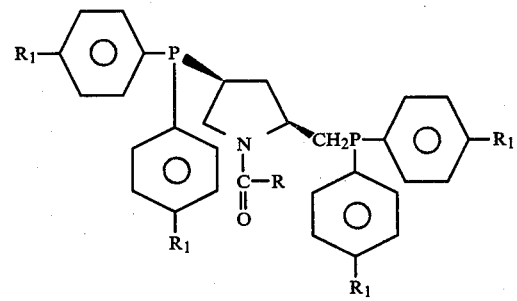

wherein R is tertiarybutoxy and R₁ is lower alkyl, lower alkoxy or

and R₃ is lower alkyl.

6. The rhodium complex of claim 5 wherein said phosphine is [2S,4S]-4-[(4,4'-dimethoxydiphenyl)phosphino]-2-[[(4,4'-dimethoxydiphenyl)phosphino]methyl]-1-pyrrolidine-1-carboxylic acid 1,1-dimethylethyl ester.

7. The rhodium complex of claim 5 wherein said phosphine is [2S,4S]-4-[4,4'-(dimethylamino)-diphenyl]-phosphino-2-[[4,4'(dimethylamino)diphenyl]phosphino]methyl-pyrrolidine-1-carboxylic acid 1,1-dimethylethyl ester.

8. The rhodium complex of claim 5 wherein said phosphine is [2S,4S]-4-[(4,4'-dimethyldiphenyl)phosphino]-2-[[(4,4'-dimethyldiphenyl)phosphino]methyl]-1-pyrrolidine-1-carboxylic acid 1,1-dimethylethyl ester.

9. A process of enantioselectively producing a compound of the formula:

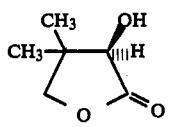

comprising hydrogenating in an organic solvent medium a compound of the formula:

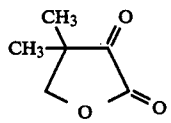

in the presence of a catalyst wherein said catalyst is a rhodium complex of a phosphine of the formula:

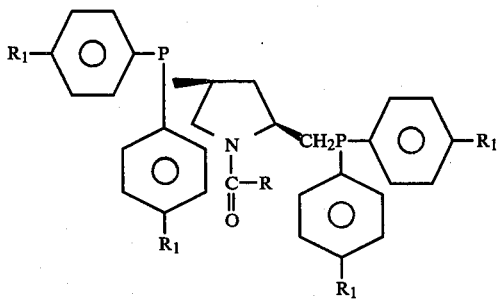

wherein R is tertiarybutoxy and R₁ is lower alkyl, lower alkoxy or

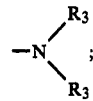

and R₃ is lower alkyl.

10. The process of claim 9 wherein said phosphine is [2S,4S]-4-[(4,4'-dimethyliphenyl)phosphino]-2-[[(4,4'-dimethyldiphenyl)phosphino]methyl]-1-pyrrolidine carboxylic acid 1,1-dimethylethyl ester.

11. The process of claim 9 wherein said phosphine is [2S,4S]-4-[[4,4'-(dimethylamino)diphenyl]phosphino]-2-[[[4,4'(dimethylamino)diphenyl]phosphino]methyl]-]pyrrolidine-1-carboxylic acid 1,1-dimethylethyl ester.

12. The process of claim 9 wherein said phosphine is [2S,4S]-4-[(4,4'-dimethoxydiphenyl)phosphino]-2-[[(4,4'-dimethoxydiphenyl)phosphino]methyl]-1-pyrrolidine-1-carboxylic acid 1,1-dimethylethyl ester.

13. The process of claim 9 wherein said complex is formed in situ in the solvent medium by adding a rhodium liberating compound and a phosphine of the formula:

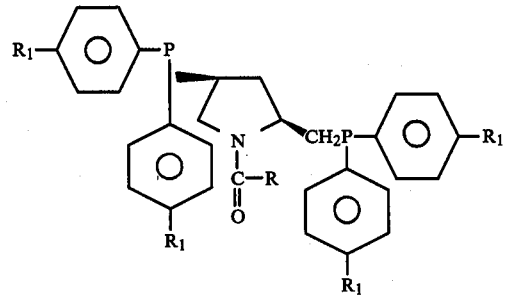

wherein R is tertiarybutoxy and R₁ is lower alkyl, lower alkoxy or

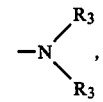

and R₃ is lower alkyl.

14. The process of claim 13 wherein said phosphine is [2S,4S]-4-[(4,4'-dimethyldiphenyl)phosphino]-2-[[(4,4'-dimethyldiphenyl)phosphino]methyl]-1-pyrrolidine carboxylic acid 1,1-dimethylethyl ester.

15. The process of claim 13 wherein said phosphine is [2S,4S]-4-[[4,4'-(dimethylamino)diphenyl]phosphino]-2-[[[4,4'(dimethylamino)diphenyl]phosphino]methyl]pyrrolidine-1-carboxylic acid 1,1-dimethylethyl ester.

* * * * *